US010653478B2

(12) United States Patent
Bloom

(10) Patent No.: US 10,653,478 B2
(45) Date of Patent: May 19, 2020

(54) DEBRIDEMENT DEVICE AND METHOD

(71) Applicant: Medtronic Advanced Energy LLC, Minneapolis, MN (US)

(72) Inventor: Eliot F. Bloom, Hopkinton, NH (US)

(73) Assignee: Medtronic Advanced Energy, LLC, Minneapolis, MN (US)

(*) Notice: Subject to any disclaimer, the term of this patent is extended or adjusted under 35 U.S.C. 154(b) by 924 days.

(21) Appl. No.: 14/951,697

(22) Filed: Nov. 25, 2015

(65) Prior Publication Data
US 2017/0143406 A1 May 25, 2017
US 2019/0183564 A9 Jun. 20, 2019

Related U.S. Application Data

(63) Continuation of application No. 13/916,127, filed on Jun. 12, 2013, now Pat. No. 9,226,792.
(Continued)

(51) Int. Cl.
*A61B 18/12* (2006.01)
*A61B 18/14* (2006.01)
(Continued)

(52) U.S. Cl.
CPC ...... *A61B 18/148* (2013.01); *A61B 17/32002* (2013.01); *A61B 18/1445* (2013.01);
(Continued)

(58) Field of Classification Search
CPC ....... A61B 18/148; A61B 18/18; A61B 17/32; A61B 17/32002; A61B 17/320016;
(Continued)

(56) References Cited

U.S. PATENT DOCUMENTS

| 2,888,928 A | 6/1959 | Seiger |
| 3,191,084 A | 6/1965 | Doka et al. |

(Continued)

FOREIGN PATENT DOCUMENTS

| EP | 1201196 | 5/2002 |
| EP | 1853187 | 11/2007 |

(Continued)

OTHER PUBLICATIONS

International Search Report and Written Opinion dated May 3, 2016 for International Application No. PCT/US2016/018486 (12 pages).
(Continued)

*Primary Examiner* — Daniel W Fowler
(74) *Attorney, Agent, or Firm* — Dicke, Billig & Czaja, PLLC

(57) ABSTRACT

Devices, systems and methods for cutting and sealing of tissue such as bone and soft tissue. Devices, systems and methods include delivery of energy including bipolar radiofrequency energy for sealing tissue which may be concurrent with delivery of fluid to a targeted tissue site. Devices include debridement devices which may include a fluid source. Devices include inner and outer shafts coaxially maintained and having cutters for debridement of tissue. An inner shaft may include electrodes apart from the cutter to minimize trauma to tissue during sealing or hemostasis. Devices may include a single, thin liner or sheath for electrically isolating the inner and outer shafts.

21 Claims, 13 Drawing Sheets

Related U.S. Application Data

(60) Provisional application No. 61/658,724, filed on Jun. 12, 2012, provisional application No. 61/704,904, filed on Sep. 24, 2012.

(51) Int. Cl.
 *A61B 18/18* (2006.01)
 *A61B 17/32* (2006.01)
 *A61B 18/00* (2006.01)

(52) U.S. Cl.
 CPC ...... *A61B 18/18* (2013.01); *A61B 2018/0063* (2013.01); *A61B 2018/00208* (2013.01); *A61B 2018/00589* (2013.01); *A61B 2018/00601* (2013.01); *A61B 2218/002* (2013.01); *A61B 2218/007* (2013.01)

(58) Field of Classification Search
 CPC ...... A61B 17/32004; A61B 17/320758; A61B 2018/00607
 See application file for complete search history.

(56) References Cited

U.S. PATENT DOCUMENTS

| | | |
|---|---|---|
| 3,223,088 A | 12/1965 | Barber et al. |
| 3,682,130 A | 8/1972 | Jeffers |
| 3,750,650 A | 8/1973 | Ruttgers |
| 3,886,944 A | 6/1975 | Jamshidi |
| 3,955,284 A | 5/1976 | Balson |
| 3,955,578 A | 5/1976 | Chamness |
| 4,014,342 A | 3/1977 | Staub |
| 4,060,088 A | 11/1977 | Morrison |
| 4,174,713 A | 11/1979 | Mehl |
| 4,195,637 A | 4/1980 | Gruntzig |
| 4,207,897 A | 6/1980 | Lloyd |
| 4,248,224 A | 2/1981 | Jones |
| 4,651,734 A | 3/1987 | Doss |
| 4,823,791 A | 4/1989 | D'Amelio et al. |
| 4,878,493 A | 11/1989 | Pasternak |
| 4,931,047 A * | 6/1990 | Broadwin ...... A61B 17/320068 604/22 |
| 4,932,952 A | 6/1990 | Wojciechowicz |
| 4,943,290 A | 7/1990 | Rexroth |
| 4,950,232 A | 8/1990 | Ruzicka |
| 4,985,030 A | 1/1991 | Melzer |
| 4,998,933 A | 3/1991 | Eggers |
| 5,112,299 A | 5/1992 | Pascaloff |
| 5,190,541 A | 3/1993 | Abele |
| 5,195,959 A | 3/1993 | Smith |
| 5,230,704 A | 7/1993 | Moberg |
| 5,234,428 A | 8/1993 | Kaufman |
| 5,254,117 A | 10/1993 | Rigby |
| 5,275,609 A | 1/1994 | Pingleton |
| 5,281,215 A | 1/1994 | Milder |
| 5,282,799 A | 2/1994 | Rydell |
| 5,330,521 A | 7/1994 | Cohen |
| 5,334,181 A | 8/1994 | Rubinsky |
| 5,336,220 A | 8/1994 | Ryan |
| 5,336,443 A | 8/1994 | Odashima |
| 5,352,222 A | 10/1994 | Rydell |
| 5,364,395 A * | 11/1994 | West, Jr. .......... A61B 17/32002 604/22 |
| 5,376,078 A | 12/1994 | Dinger |
| 5,383,874 A | 1/1995 | Jackson |
| 5,385,148 A | 1/1995 | Lesh |
| 5,395,312 A | 3/1995 | Desai |
| 5,401,272 A | 3/1995 | Perkins |
| 5,405,348 A | 4/1995 | Anspach |
| 5,405,376 A | 4/1995 | Mulier |
| 5,413,556 A | 5/1995 | Whittingham |
| 5,417,709 A | 5/1995 | Slater |
| 5,431,168 A | 7/1995 | Webster |
| 5,431,649 A | 7/1995 | Mulier |
| 5,441,503 A | 8/1995 | Considine |
| 5,443,463 A | 8/1995 | Stern |
| 5,445,638 A | 8/1995 | Rydell |
| 5,460,629 A | 10/1995 | Shlain |
| 5,490,819 A | 2/1996 | Nicholas |
| 5,492,527 A | 2/1996 | Glowa |
| 5,496,271 A | 3/1996 | Burton |
| 5,505,700 A | 4/1996 | Leone |
| 5,540,562 A | 7/1996 | Giter |
| 5,540,708 A | 7/1996 | Lim |
| 5,542,196 A | 8/1996 | Kantro |
| 5,542,945 A | 8/1996 | Fritzsch |
| 5,556,397 A | 9/1996 | Long |
| 5,560,373 A | 10/1996 | De Santis |
| 5,562,702 A | 10/1996 | Huitema |
| 5,569,243 A | 10/1996 | Kortenbach |
| 5,569,254 A | 10/1996 | Carlson |
| 5,573,424 A | 11/1996 | Poppe |
| 5,595,183 A | 1/1997 | Swanson |
| 5,599,346 A | 2/1997 | Edwards |
| 5,605,539 A | 2/1997 | Buelna |
| 5,609,573 A | 3/1997 | Sandock |
| 5,620,415 A | 4/1997 | Lucey |
| 5,620,447 A | 4/1997 | Smith |
| 5,647,869 A | 7/1997 | Goble |
| 5,676,693 A | 10/1997 | LaFontaine |
| 5,685,838 A | 11/1997 | Peters |
| 5,688,267 A | 11/1997 | Panescu |
| 5,697,536 A | 12/1997 | Eggers |
| 5,712,543 A | 1/1998 | Sjostrom |
| 5,713,942 A | 2/1998 | Stern |
| 5,733,280 A | 3/1998 | Avitall |
| 5,743,903 A | 4/1998 | Stern |
| 5,766,167 A | 6/1998 | Eggers |
| 5,792,167 A | 8/1998 | Kablik |
| 5,797,905 A | 8/1998 | Fleischman |
| 5,797,960 A | 8/1998 | Stevens |
| 5,810,764 A | 9/1998 | Eggers |
| 5,810,802 A | 9/1998 | Panescu |
| 5,810,809 A | 9/1998 | Rydell |
| 5,814,044 A | 9/1998 | Hooven |
| 5,827,216 A | 10/1998 | Igo |
| 5,836,947 A | 11/1998 | Fleischman |
| 5,840,030 A | 11/1998 | Ferek Petric |
| 5,843,021 A | 12/1998 | Edwards |
| 5,843,152 A | 12/1998 | Tu |
| 5,849,023 A | 12/1998 | Mericle |
| 5,873,855 A | 2/1999 | Eggers |
| 5,873,886 A | 2/1999 | Larsen |
| 5,891,142 A | 4/1999 | Eggers |
| 5,895,355 A | 4/1999 | Schaer |
| 5,897,553 A | 4/1999 | Mulier |
| 5,899,915 A | 5/1999 | Saadat |
| 5,902,272 A | 5/1999 | Eggers et al. |
| 5,904,681 A | 5/1999 | West, Jr. |
| 5,913,854 A | 6/1999 | Maguire |
| 5,916,150 A | 6/1999 | Sillman |
| 5,916,213 A | 6/1999 | Haissaguerre |
| 5,921,982 A | 7/1999 | Lesh |
| 5,925,045 A | 7/1999 | Reimels |
| 5,927,284 A | 7/1999 | Borst |
| 5,928,191 A | 7/1999 | Houser |
| 5,935,123 A | 8/1999 | Edwards |
| 5,941,876 A | 8/1999 | Nardella |
| 5,944,715 A | 8/1999 | Goble |
| 5,957,881 A | 9/1999 | Peters |
| 5,957,919 A | 9/1999 | Laufer |
| 5,971,980 A | 10/1999 | Sherman |
| 5,971,983 A | 10/1999 | Lesh |
| 5,980,516 A | 11/1999 | Mulier |
| 5,989,248 A | 11/1999 | Tu |
| 5,993,412 A | 11/1999 | Deily |
| 6,004,316 A | 12/1999 | Laufer |
| 6,004,319 A | 12/1999 | Goble |
| 6,010,476 A | 1/2000 | Saadat |
| 6,010,500 A | 1/2000 | Sherman |
| 6,012,457 A | 1/2000 | Lesh |
| 6,015,391 A | 1/2000 | Rishton |
| 6,024,733 A | 2/2000 | Eggers |
| 6,042,556 A | 3/2000 | Beach |

(56) References Cited

U.S. PATENT DOCUMENTS

| | | | |
|---|---|---|---|
| 6,042,593 A | 3/2000 | Storz |
| 6,053,923 A | 4/2000 | Veca |
| 6,063,081 A | 5/2000 | Mulier |
| 6,071,279 A | 6/2000 | Whayne |
| 6,074,386 A | 6/2000 | Goble |
| 6,088,894 A | 7/2000 | Oakley |
| 6,096,037 A | 8/2000 | Mulier |
| 6,117,101 A | 9/2000 | Diederich |
| 6,142,993 A | 11/2000 | Whayne |
| 6,142,994 A | 11/2000 | Swanson |
| 6,152,920 A | 11/2000 | Thompson |
| 6,152,941 A | 11/2000 | Himes |
| 6,161,543 A | 12/2000 | Cox |
| 6,165,174 A | 12/2000 | Jacobs |
| 6,193,715 B1 | 2/2001 | Wrublewski |
| 6,197,024 B1 | 3/2001 | Sullivan |
| 6,214,003 B1 | 4/2001 | Morgan |
| 6,217,528 B1 | 4/2001 | Koblish |
| 6,217,576 B1 | 4/2001 | Tu |
| 6,217,598 B1 | 4/2001 | Berman |
| 6,221,088 B1 | 4/2001 | Bays |
| 6,224,592 B1 | 5/2001 | Eggers |
| 6,231,518 B1 | 5/2001 | Grabek |
| 6,235,024 B1 | 5/2001 | Tu |
| 6,237,605 B1 | 5/2001 | Vaska |
| 6,238,347 B1 | 5/2001 | Nix |
| 6,238,393 B1 | 5/2001 | Mulier |
| 6,245,061 B1 | 6/2001 | Panescu |
| 6,245,064 B1 | 6/2001 | Lesh |
| 6,245,065 B1 | 6/2001 | Panescu |
| 6,246,638 B1 | 6/2001 | Zook |
| 6,251,092 B1 | 6/2001 | Qin |
| 6,251,128 B1 | 6/2001 | Knopp |
| 6,270,471 B1 | 8/2001 | Hechel |
| 6,292,689 B1 | 9/2001 | Wallace |
| 6,293,943 B1 | 9/2001 | Panescu |
| 6,293,957 B1 | 9/2001 | Peters |
| 6,296,638 B1 | 10/2001 | Davison |
| 6,325,797 B1 | 12/2001 | Stewart |
| 6,328,736 B1 | 12/2001 | Mulier |
| 6,332,881 B1 | 12/2001 | Carner |
| 6,358,248 B1 | 3/2002 | Mulier |
| 6,361,531 B1 | 3/2002 | Hissong |
| 6,364,876 B1 | 4/2002 | Erb |
| 6,368,275 B1 | 4/2002 | Sliwa |
| 6,383,151 B1 | 5/2002 | Diederich |
| 6,385,472 B1 | 5/2002 | Hall |
| 6,398,792 B1 | 6/2002 | O'Connor |
| 6,409,722 B1 | 6/2002 | Hoey |
| 6,413,254 B1 | 7/2002 | Hissong |
| 6,419,648 B1 | 7/2002 | Vitek |
| 6,425,867 B1 | 7/2002 | Vaezy |
| 6,430,426 B2 | 8/2002 | Avitall |
| 6,440,130 B1 | 8/2002 | Mulier |
| 6,443,952 B1 | 9/2002 | Mulier |
| 6,454,782 B1 | 9/2002 | Schwemberger |
| 6,461,357 B1 | 10/2002 | Sharkey |
| 6,471,697 B1 | 10/2002 | Lesh |
| 6,471,698 B1 | 10/2002 | Edwards |
| 6,474,340 B1 | 11/2002 | Vaska |
| 6,475,216 B2 | 11/2002 | Mulier |
| 6,477,396 B1 | 11/2002 | Mest |
| 6,484,727 B1 | 11/2002 | Vaska |
| 6,488,678 B2 | 12/2002 | Sherman |
| 6,488,680 B1 | 12/2002 | Franischelli |
| 6,494,892 B1 | 12/2002 | Ireland |
| 6,502,575 B1 | 1/2003 | Jacobs |
| 6,503,263 B2 | 1/2003 | Adams |
| 6,514,250 B1 | 2/2003 | Jahns |
| 6,527,767 B2 | 3/2003 | Wang |
| 6,537,248 B2 | 3/2003 | Mulier |
| 6,537,272 B2 | 3/2003 | Christopherson |
| 6,558,382 B2 | 5/2003 | Jahns |
| 6,558,385 B1 | 5/2003 | McClurken |
| 6,565,560 B1 | 5/2003 | Goble |
| 6,565,561 B1 | 5/2003 | Goble |
| 6,584,360 B2 | 6/2003 | Francischelli |
| 6,585,732 B2 | 7/2003 | Mulier |
| 6,605,084 B2 | 8/2003 | Acker |
| 6,610,055 B1 | 8/2003 | Swanson |
| 6,610,059 B1 | 8/2003 | West, Jr. |
| 6,610,060 B2 | 8/2003 | Mulier |
| 6,613,048 B2 | 9/2003 | Mulier |
| 6,623,500 B1 | 9/2003 | Cook et al. |
| 6,645,199 B1 | 11/2003 | Jenkins |
| 6,648,883 B2 | 11/2003 | Francischelli |
| 6,656,175 B2 | 12/2003 | Francischelli |
| 6,663,627 B2 | 12/2003 | Francischelli |
| 6,663,628 B2 | 12/2003 | Peters |
| 6,689,131 B2 | 2/2004 | McClurken |
| 6,699,240 B2 | 3/2004 | Francischelli |
| 6,702,810 B2 | 3/2004 | McClurken |
| 6,702,811 B2 | 3/2004 | Stewart |
| 6,706,038 B2 | 3/2004 | Francischelli |
| 6,706,039 B2 | 3/2004 | Mulier |
| 6,716,211 B2 | 4/2004 | Mulier |
| 6,716,215 B1 | 4/2004 | David |
| 6,736,810 B2 | 5/2004 | Hoey |
| 6,752,816 B2 | 6/2004 | Culp |
| 6,755,827 B2 | 6/2004 | Mulier |
| 6,764,487 B2 | 7/2004 | Mulier |
| 6,773,433 B2 | 8/2004 | Stewart |
| 6,776,780 B2 | 8/2004 | Mulier |
| 6,780,180 B1 | 8/2004 | Goble |
| 6,807,968 B2 | 10/2004 | Francischelli |
| 6,824,550 B1 | 11/2004 | Noriega |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart |
| 6,911,019 B2 | 6/2005 | Mulier |
| 6,916,318 B2 | 7/2005 | Francischelli |
| 6,923,803 B2 | 8/2005 | Goble |
| 6,936,046 B2 | 8/2005 | Hissong |
| 6,949,097 B2 | 9/2005 | Stewart |
| 6,949,098 B2 | 9/2005 | Mulier |
| 6,953,461 B2 | 10/2005 | McClurken |
| 6,960,205 B2 | 11/2005 | Jahns |
| 6,962,589 B2 | 11/2005 | Mulier |
| 6,979,332 B2 | 12/2005 | Adams |
| 7,052,494 B2 | 5/2006 | Goble |
| 7,115,139 B2 | 10/2006 | McClurken |
| 7,150,747 B1 | 12/2006 | McDonald |
| 7,166,103 B2 | 1/2007 | Carmel |
| 7,179,255 B2 | 2/2007 | Lettice |
| 7,229,437 B2 | 6/2007 | Johnson |
| 7,232,440 B2 | 6/2007 | Dumbauld |
| 7,237,990 B2 | 7/2007 | Deng |
| 7,247,155 B2 | 7/2007 | Hoey |
| 7,247,161 B2 | 7/2007 | Johnston |
| 7,261,711 B2 | 8/2007 | Mulier |
| 7,276,074 B2 | 10/2007 | Adams |
| 7,278,994 B2 | 10/2007 | Goble |
| 7,309,325 B2 | 12/2007 | Mulier |
| 7,311,708 B2 | 12/2007 | McClurken |
| 7,322,974 B2 | 1/2008 | Swoyer |
| 7,361,175 B2 | 4/2008 | Suslov |
| 7,364,579 B2 | 4/2008 | Mulier |
| 7,416,539 B2 | 8/2008 | Johnston |
| 7,442,191 B2 | 10/2008 | Hovda |
| 7,537,595 B2 | 5/2009 | McClurken |
| 7,604,635 B2 | 10/2009 | McClurken |
| 7,608,072 B2 | 10/2009 | Swanson |
| 7,645,277 B2 | 1/2010 | McClurken |
| 7,651,494 B2 | 1/2010 | McClurken |
| 7,674,263 B2 | 3/2010 | Ryan |
| 7,691,050 B2 | 4/2010 | Gellman |
| 7,699,846 B2 * | 4/2010 | Ryan ............... A61B 17/32002 606/170 |
| 7,736,361 B2 | 6/2010 | Palanker |
| 7,749,608 B2 | 7/2010 | Laude |
| 7,785,337 B2 | 8/2010 | Adams |
| 7,811,282 B2 | 10/2010 | McClurken |

(56) References Cited

U.S. PATENT DOCUMENTS

| | | |
|---|---|---|
| 7,815,634 B2 | 10/2010 | McClurken |
| 7,854,736 B2 | 12/2010 | Ryan |
| 7,909,820 B2 | 3/2011 | Lipson |
| 7,942,872 B2 | 5/2011 | Em-Gal Moshe |
| 7,976,544 B2 | 7/2011 | McClurken |
| 7,993,337 B2 | 8/2011 | Lesh |
| 7,997,278 B2 | 8/2011 | Utley |
| 7,998,140 B2 | 8/2011 | McClurken |
| 8,012,153 B2 | 9/2011 | Woloszko |
| 8,034,071 B2 | 10/2011 | Scribner |
| 8,038,670 B2 | 10/2011 | McClurken |
| 8,048,070 B2 | 11/2011 | O'Brien |
| 8,083,736 B2 | 12/2011 | McClurken |
| 8,105,323 B2 | 1/2012 | Buysse |
| 8,109,956 B2 | 2/2012 | Shadeck |
| 8,172,828 B2 | 5/2012 | Chang |
| 8,177,783 B2 | 5/2012 | Davison |
| 8,202,288 B2 | 6/2012 | Adams |
| 8,216,233 B2 | 7/2012 | McClurken |
| 8,277,474 B2 | 10/2012 | Norman et al. |
| 8,317,786 B2 | 11/2012 | Dahla |
| 8,323,276 B2 | 12/2012 | Palanker |
| 8,348,946 B2 | 1/2013 | McClurken |
| 8,361,068 B2 | 1/2013 | McClurken |
| 8,377,086 B2 | 2/2013 | Flynn |
| 8,388,642 B2 | 3/2013 | Muni |
| 8,414,572 B2 | 4/2013 | Davison |
| 8,568,419 B2 | 10/2013 | de Wekker |
| 9,226,792 B2 | 1/2016 | Bloom |
| 2001/0047183 A1 | 11/2001 | Privitera |
| 2002/0038129 A1 | 3/2002 | Peters |
| 2002/0049483 A1 | 4/2002 | Knowlton |
| 2002/0062131 A1 | 5/2002 | Gallo |
| 2002/0082643 A1 | 6/2002 | Milla |
| 2002/0165549 A1 | 11/2002 | Owusu Akyaw |
| 2003/0014050 A1 | 1/2003 | Sharkey |
| 2003/0032954 A1 | 2/2003 | Carranza |
| 2003/0045872 A1 | 3/2003 | Jacobs |
| 2003/0073993 A1 | 4/2003 | Ciarrocca |
| 2003/0097129 A1 | 5/2003 | Davison |
| 2003/0144656 A1 | 7/2003 | Ocel |
| 2003/0165794 A1 | 9/2003 | Matoba |
| 2003/0191462 A1 | 10/2003 | Jacobs |
| 2003/0204185 A1 | 10/2003 | Sherman |
| 2003/0216724 A1 | 11/2003 | Jahns |
| 2004/0010258 A1 | 1/2004 | Carusillo |
| 2004/0015106 A1 | 1/2004 | Coleman |
| 2004/0015219 A1 | 1/2004 | Francischelli |
| 2004/0024395 A1 | 2/2004 | Ellman |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart |
| 2004/0087940 A1 | 5/2004 | Jahns |
| 2004/0092926 A1 | 5/2004 | Hoey |
| 2004/0111136 A1 | 6/2004 | Sharkey |
| 2004/0111137 A1 | 6/2004 | Shankey |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0167427 A1 | 8/2004 | Quick |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0243163 A1 | 12/2004 | Casiano |
| 2004/0267326 A1 | 12/2004 | Ocel |
| 2005/0010095 A1 | 1/2005 | Stewart |
| 2005/0033280 A1 | 2/2005 | Francischelli |
| 2005/0090815 A1 | 4/2005 | Francischelli |
| 2005/0090816 A1 | 4/2005 | McClurken |
| 2005/0143729 A1 | 6/2005 | Francischelli |
| 2005/0165392 A1 | 7/2005 | Francischelli |
| 2005/0171525 A1 | 8/2005 | Rioux |
| 2005/0209564 A1 | 9/2005 | Bonner |
| 2005/0222566 A1 | 10/2005 | Nakahira |
| 2005/0267454 A1 | 12/2005 | Hissong |
| 2005/0277970 A1 | 12/2005 | Norman |
| 2006/0009756 A1 | 1/2006 | Francischelli |
| 2006/0009759 A1 | 1/2006 | Chrisitian |
| 2006/0064085 A1 | 3/2006 | Schechter |
| 2006/0106375 A1 | 5/2006 | Werneth |
| 2006/0178670 A1* | 8/2006 | Woloszko ......... A61B 18/1402 606/48 |
| 2006/0200123 A1* | 9/2006 | Ryan .................. A61B 18/148 606/48 |
| 2006/0259055 A1 | 11/2006 | Thorne |
| 2007/0049920 A1 | 3/2007 | McClurken |
| 2007/0093808 A1 | 4/2007 | Mulier |
| 2007/0100336 A1 | 5/2007 | McFarlin et al. |
| 2007/0118114 A1 | 5/2007 | Miller |
| 2007/0149965 A1 | 6/2007 | Gallo |
| 2007/0179495 A1 | 8/2007 | Mitchell |
| 2007/0208332 A1 | 9/2007 | Mulier |
| 2008/0015563 A1 | 1/2008 | Hoey |
| 2008/0042513 A1 | 2/2008 | Kuenzel et al. |
| 2008/0058796 A1 | 3/2008 | O'Brien |
| 2008/0071270 A1 | 3/2008 | Desinger |
| 2008/0132890 A1 | 6/2008 | Woloszko et al. |
| 2008/0207028 A1 | 8/2008 | Schutz |
| 2008/0262489 A1 | 10/2008 | Steinke |
| 2009/0118729 A1 | 5/2009 | Auth |
| 2009/0264879 A1 | 10/2009 | McClurken |
| 2009/0270896 A1 | 10/2009 | Sullivan |
| 2009/0306655 A1 | 12/2009 | Stangenes |
| 2010/0087812 A1 | 4/2010 | Davison |
| 2010/0100095 A1 | 4/2010 | McClurken |
| 2010/0160906 A1 | 6/2010 | Jarrard |
| 2010/0241178 A1 | 9/2010 | Tilson |
| 2010/0298763 A1 | 11/2010 | Adams |
| 2010/0298855 A1 | 11/2010 | Dierck |
| 2010/0317998 A1 | 12/2010 | Hibner |
| 2011/0009856 A1 | 1/2011 | Jorgensen |
| 2011/0017801 A1 | 1/2011 | Zemlok |
| 2011/0028965 A1 | 2/2011 | McClurken |
| 2011/0066142 A1 | 3/2011 | Tal |
| 2011/0137298 A1 | 6/2011 | Nguyen |
| 2011/0178515 A1 | 7/2011 | Bloom |
| 2011/0196367 A1 | 8/2011 | Gallo |
| 2011/0295249 A1 | 12/2011 | Bloom |
| 2011/0301578 A1* | 12/2011 | Muniz-Medina ........................ A61B 17/32002 606/1 |
| 2011/0319889 A1 | 12/2011 | Conley |
| 2012/0004657 A1 | 1/2012 | Conley |
| 2012/0071712 A1 | 3/2012 | Manwaring |
| 2012/0101496 A1 | 4/2012 | McClurken |
| 2012/0109130 A1 | 5/2012 | Casey |
| 2012/0116261 A1 | 5/2012 | Mumaw et al. |
| 2012/0116397 A1 | 5/2012 | Rencher |
| 2012/0143293 A1 | 6/2012 | Mauch |
| 2012/0150165 A1 | 6/2012 | Conley |
| 2012/0157989 A1 | 6/2012 | Stone |
| 2012/0172877 A1 | 7/2012 | Ryan |
| 2012/0179158 A1 | 7/2012 | Stierman |
| 2012/0184983 A1 | 7/2012 | Chang |
| 2012/0191084 A1 | 7/2012 | Davison |
| 2012/0191117 A1* | 7/2012 | Palmer ............... A61B 10/0275 606/170 |
| 2012/0215245 A1 | 8/2012 | Palmer |
| 2012/0221035 A1 | 8/2012 | Harvey |
| 2012/0253343 A1 | 10/2012 | McClurken |
| 2012/0330272 A1* | 12/2012 | Nilsson ............. A61M 5/14244 604/500 |
| 2012/0330292 A1* | 12/2012 | Shadduck ............ A61B 18/18 606/13 |
| 2013/0004595 A1 | 1/2013 | Bhatia |
| 2013/0053830 A1 | 2/2013 | Edwards |
| 2013/0085498 A1 | 4/2013 | Matusaitis |
| 2013/0331833 A1* | 12/2013 | Bloom ............... A61B 18/1445 606/33 |
| 2013/0345704 A1 | 12/2013 | Palmer |

(56) References Cited

U.S. PATENT DOCUMENTS

| | | |
|---|---|---|
| 2014/0005700 A1 | 1/2014 | Casey |
| 2014/0100567 A1 | 4/2014 | Edwards |
| 2014/0132126 A1 | 5/2014 | Vicars et al. |
| 2014/0155888 A1 | 6/2014 | Edwards |
| 2014/0155889 A1 | 6/2014 | Edwards |
| 2014/0155923 A1 | 6/2014 | Edwards |
| 2014/0207217 A1 | 7/2014 | Lischinsky et al. |
| 2014/0276808 A1 | 9/2014 | Gittard et al. |
| 2014/0277036 A1 | 9/2014 | Flynn |
| 2015/0265337 A1 | 9/2015 | Bloom |
| 2016/0235468 A1 | 8/2016 | Prisco et al. |
| 2016/0235469 A1 | 8/2016 | Prisco et al. |
| 2016/0235474 A1 | 8/2016 | Prisco et al. |

FOREIGN PATENT DOCUMENTS

| | | |
|---|---|---|
| EP | 2044893 | 4/2009 |
| EP | 2133028 | 12/2009 |
| GB | 247060 | 12/2010 |
| WO | WO1996/037156 | 11/1996 |
| WO | WO1997/023169 | 7/1997 |
| WO | WO1998/034550 | 8/1998 |
| WO | WO1998/038932 | 9/1998 |
| WO | WO2003/079911 | 10/2003 |
| WO | WO2011/037664 | 3/2011 |
| WO | WO2012/102838 | 8/2012 |
| WO | 2013191811 | 12/2013 |
| WO | WO2014/084983 | 6/2014 |
| WO | WO2014/133663 | 9/2014 |

OTHER PUBLICATIONS

Non-Final Office Action for U.S. Appl. No. 15/046,853 dated Apr. 12, 2018 (38 pages).
Non-Final Office Action for U.S. Appl. No. 15/046,869 dated Mar. 28, 2018 (29 pages).
Non-Final Office Action for U.S. Appl. No. 15/047,242 dated Jul. 10, 2018 (32 pages).
Non-Final Office Action for U.S. Appl. No. 15/046,853 dated Oct. 25, 2018 (39 pages).
Final Office Action for U.S. Appl. No. 15/047,242 dated Jan. 25, 2019 (20 pages).
Notice of Allowance for U.S. Appl. No. 15/046,869 dated Oct. 9, 2018 (23 pages).
Notice of Allowance for U.S. Appl. No. 15/046,853 dated Apr. 3, 2019 (11 pages).
Non-Final Office Action for U.S. Appl. No. 15/047,242 dated Apr. 11, 2019 (28 pages).
Non-Final Office Action for U.S. Appl. No. 15/047,242 dated Aug. 21, 2019 (14 pages).
Final Office Action for U.S. Appl. No. 15/047,242 dated Feb. 21, 2020 (11 pages).

* cited by examiner

DEBRIDEMENT DEVICE AND METHOD

CROSS-REFERENCE TO RELATED APPLICATIONS

This application is a continuation of U.S. application Ser. No. 13/916,127, filed on Jun. 12, 2013, which claims the benefit of U.S. provisional application 61/658,724, filed Jun. 12, 2012 and of U.S. Provisional Application 61/704,904, filed Sep. 24, 2012, the entire disclosures of which are hereby incorporated by reference in their respective entireties.

BACKGROUND

The present invention is generally directed to devices, systems and methods for cutting and sealing tissue such as bone and soft tissue. The present invention may be particularly suitable for sinus applications and nasopharyngeal/laryngeal procedures and may combine or provide Transcollation® technology with a microdebrider device.

Devices, systems and methods according to the present disclosure may be suitable for a variety of procedures including ear, nose and throat (ENT) procedures, head and neck procedures, otology procedures, including otoneurologic procedures. The present disclosure may be suitable for a varient of other surgical procedures including mastoidectomies and mastoidotomies; nasopharyngeal and laryngeal procedures such as tonsillectomies, trachael procedures, adenoidectomies, laryngeal lesion removal, and polypectomies; for sinus procedures such as polypectomies, septoplasties, removals of septal spurs, anstrostomies, frontal sinus trephination and irrigation, frontal sinus opening, endoscopic DCR, correction of deviated septums and transsphenoidal procedures; rhinoplasty and removal of fatty tissue in the maxillary and mandibular regions of the face.

Sinus surgery is challenging due to its location to sensitive organs such as the eyes and brain, the relatively small size of the anatomy of interest to the surgeon, and the complexity of the typical procedures. Examples of debriders with mechanical cutting components are described in U.S. Pat. Nos. 5,685,838; 5,957,881 and 6,293,957. These devices are particularly successful for powered tissue cutting and removal during sinus surgery, but do not include any mechanism for sealing tissue to reduce the amount of bleeding from the procedure. Sealing tissue is especially desirable during sinus surgery which tends to be a complex and precision oriented practice.

Electrosurgical technology was introduced in the 1920's. In the late 1960's, isolated generator technology was introduced. In the late 1980's, the effect of RF lesion generation was well known. See e.g., Cosman et al., *Radiofrequency lesion generation and its effect on tissue impedance*, Applied Neurophysiology (1988) 51: 230-242. Radiofrequency ablation is successfully used in the treatment of unresectable solid tumors in the liver, lung, breast, kidney, adrenal glands, bone, and brain tissue. See e.g., Thanos et al., *Image-Guided Radiofrequency Ablation of a Pancreatic Tumor with a New Triple Spiral-Shaped Electrode*, Cardiovasc. Intervent. Radiol. (2010) 33:215-218.

The use of RF energy to ablate tumors or other tissue is known. See e.g., McGahan J P, Brock J M, Tesluk H et al., *Hepatic ablation with use of radio-frequency electrocautery in the animal model*. J Vasc Interv Radiol 1992; 3:291-297. Products capable of aggressive ablation can sometimes leave undesirable charring on tissue or stick to the tissue during a surgical procedure. Medical devices that combine mechanical cutting and an electrical component for cutting, ablating or coagulating tissue are described, for example, in U.S. Pat. Nos. 4,651,734 and 5,364,395.

Commercial medical devices that include monopolar ablation systems include the Invatec MIRAS RC, MIRAS TX and MIRAS LC systems previously available from Invatec of Italy. These systems included a probe, a grounding pad on the patient and a generator that provides energy in the range of 450 to 500 kHz. Other examples of RF bipolar ablation components for medical devices are disclosed in U.S. Pat. Nos. 5,366,446 and 5,697,536.

Medical devices are also used to ablate heart tissue with RF energy. See, e.g., Siefert et al. *Radiofrequency Maze Ablation for Atrial Fibrillation*, Circulation 90(4): I-594. Some patents describing RF ablation of heart tissue include U.S. Pat. Nos. 5,897,553, 6,063,081 and 6,165,174. Devices for RF ablation of cardiac tissue are typically much less aggressive than RF used to cut tissue as in many procedures on cardiac tissue, a surgeon only seeks to kill tissue instead of cutting or removing the tissue. Cardiac ablation of this type seeks to preserve the structural integrity of the cardiac tissue, but destroy the tissue's ability to transfer aberrant electrical signals that can disrupt the normal function of the heart.

Transcollation® technology, for example, the sealing energy supplied by the Aquamantys® System (available from Medtronic Advanced Energy of Portsmouth, N.H.) is a patented technology which stops bleeding and reduces blood loss during and after surgery and is a combination of radiofrequency (RF) energy and saline that provides hemostatic sealing of soft tissue and bone and may lower transfusion rates and reduce the need for other blood management products during or after surgery. Transcollation® technology integrates RF energy and saline to deliver controlled thermal energy to tissue. Coupling of saline and RF energy allows a device temperature to stay in a range which produces a tissue effect without the associated charring found in other ablation methods.

Other ablation devices include both mechanical cutting as well as ablation energy. For example, the PK Diego® powered dissector is commercially available from Gyms ENT of Bartlett, Tenn. This device utilizes two mechanical cutting blade components that are moveable relative to each other, one of which acts as an electrode in a bipolar ablation system. The distal end portion of the device includes six layers to accomplish mechanical cutting and electrical coagulation. The dual use of one of the components as both a mechanical, oscillating cutting element and a portion of the bipolar system of the device is problematic for several reasons. First, the arrangement exposes the sharp mechanical cutting component to tissue just when hemostasis is sought. In addition, the electrode arrangement does not provide for optimal application of energy for hemostasis since the energy is applied essentially at a perimeter or outer edge of a cut tissue area rather than being applied to a central location of the cut tissue. The arrangement of the device also requires more layers than necessary in the construction of a device with both sharp cutters and RF ablation features. The overabundance of layers can make it difficult to design a small or optimally-sized distal end. Generally speaking, the larger the distal end, the more difficult it is for the surgeon to visualize the working surfaces of the device. The use of six layers at the distal end of the system also interferes with close intimate contact between the tissue and the electrodes. Some examples of cutting devices are described in U.S. Pat. Nos. 7,854,736 and 7,674,263.

The Medtronic Straightshot® M4 Microdebrider uses sharp cutters to cut tissue, and suction to withdraw tissue. While tissue debridement with the Medtronic microdebrider system is a simple and safe technique, some bleeding may occur. The Medtronic microdebrider does not include a feature dedicated to promoting hemostasis or bleeding management. Thus, nasal packing is often used.

BRIEF DESCRIPTION OF THE DRAWINGS

In the drawings, where like numerals refer to like components throughout several views.

DETAILED DESCRIPTION

Figure 1:
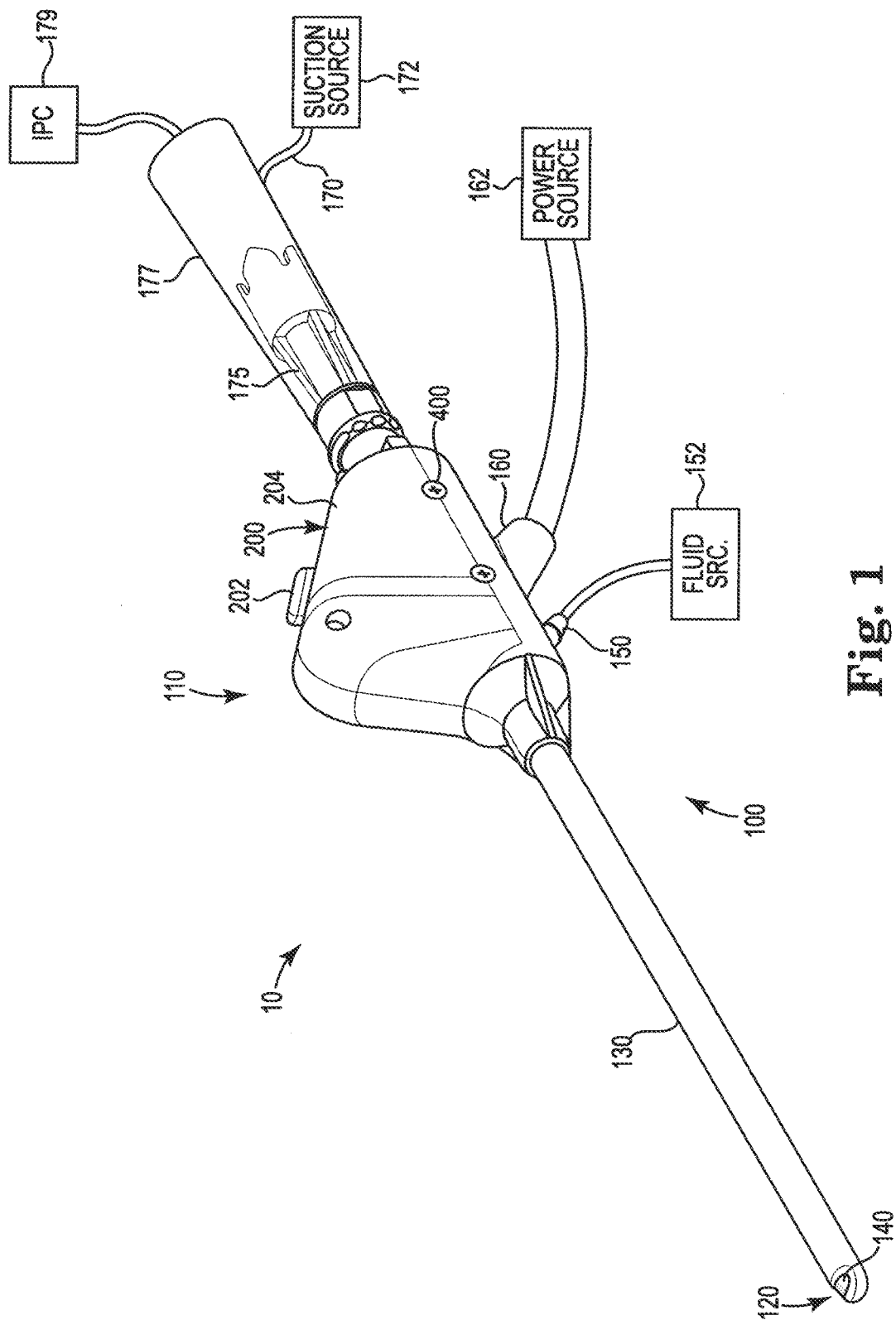
FIG. 1 is a perspective view of a system according to one aspect of the present invention.

FIG. 1 illustrates a system 10 according to an aspect of the present invention. The system 10 includes a device 100 having a distal end region indicated generally at 120 and a proximal end region indicated generally at 110. The device includes an outer shaft 130 and an inner shaft 140 coaxially maintained within the outer shaft 130. A portion of the inner shaft 140 is shown in FIG. 1 at distal end region 120. Proximal end region 110 includes a button activation cell 200 comprising a housing 204 and a button 202, the proximal end region further comprising a hub 175 coupled to inner shaft 140. The hub is configured to couple to a handle or handpiece 177 which can be manipulated by a user (e.g., a surgeon). The handpiece 177, in turn may be coupled to an integrated power console or IPC 179 for driving the device 100 and specifically for controlling rotation of inner shaft 140. The IPC 179 may also include a fluid source (not shown) and may provide fluid delivery to device 100.

Proximal end region 110 also includes a fluid source connector 150, a power source connector 160 and a suction source connector 170 for connection to a fluid source 152, a power source, 162 and/or a suction source of system 10. One fluid useful with the present disclosure is saline, however, other fluids are contemplated. Power source 162 may be a generator and optionally may be designed for use with bipolar energy or a bipolar energy supply. For example, the Transcollation® sealing energy supplied by the Aquamantys® System (available from Medtronic Advanced Energy of Portsmouth, N.H.) may be used. Both the fluid source 152 and suction source 172 are optional components of system 10. However, use of fluid in conjunction with energy delivery aids in providing optimal tissue effect as will be further explained, thus embodiments of the present invention include specific arrangement of the device 100 for coupling of energy with a fluid. In use, a fluid (e.g., saline) may be emitted from an opening at the distal end region of the device 100. Tissue fragments and fluids can be removed from a surgical site through an opening (not shown in FIG. 1) in the distal end region via the suction source 172, as will be further explained below.

Figure 2:
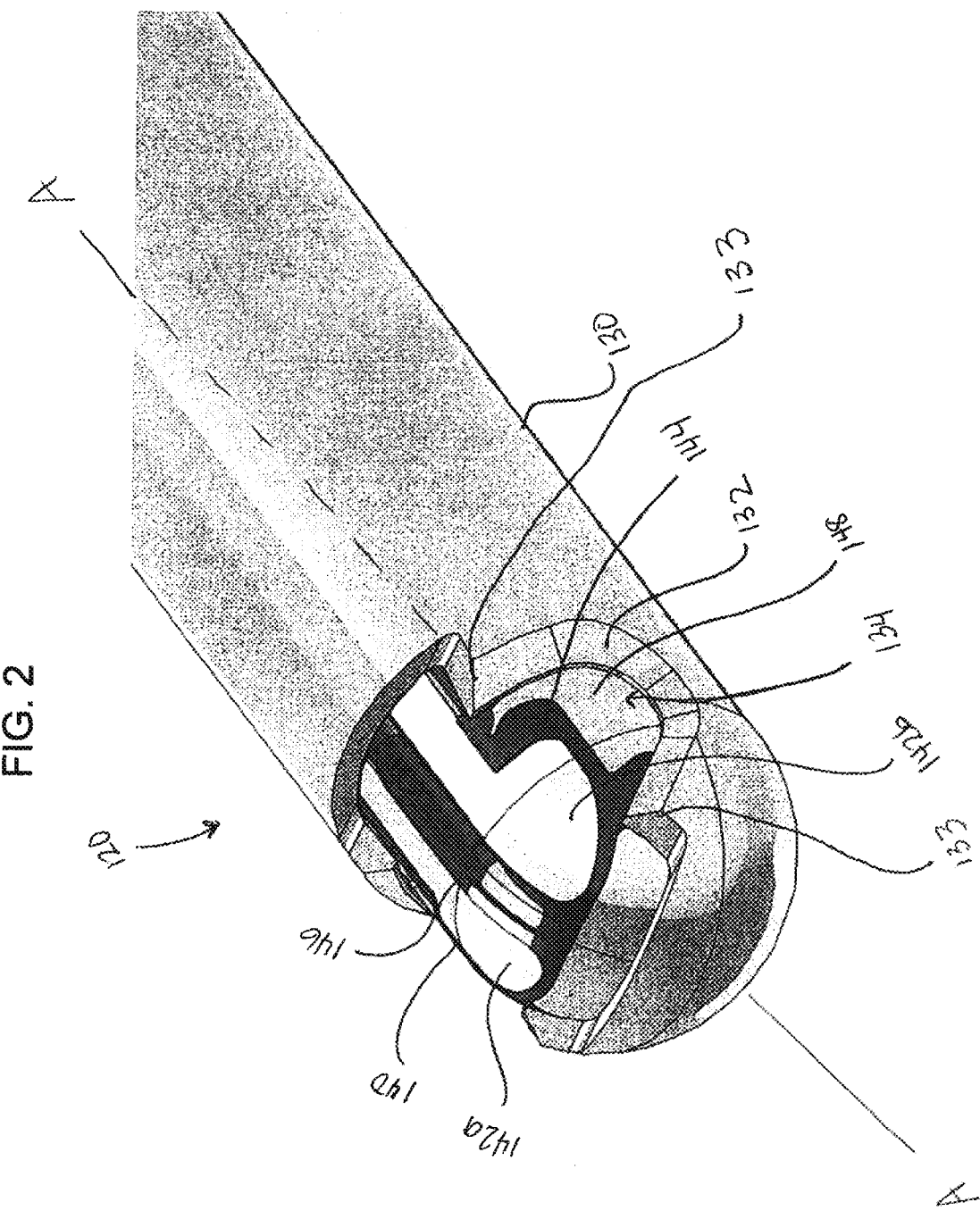
FIG. 2 is a perspective view of a distal end region of a device with an inner shaft in a position according to one aspect of the present invention.
Figure 3:
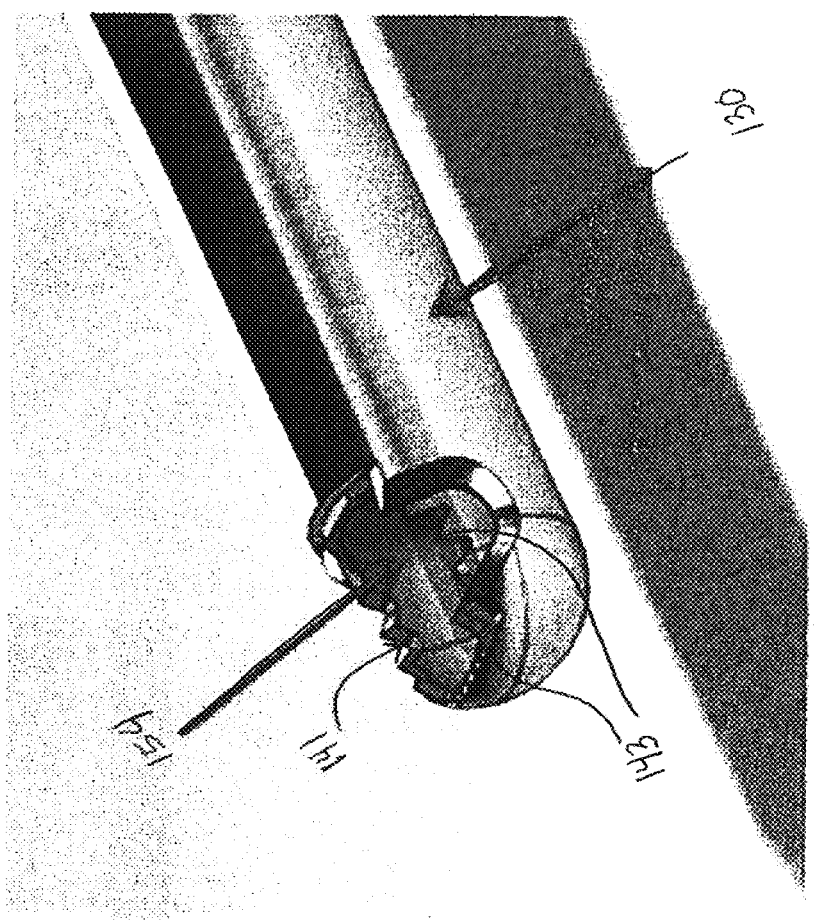
FIG. 3 is a perspective view of the distal end region of a device with an inner shaft in an alternative position according to one aspect of the present invention.

FIG. 2 shows an enlarged perspective view of distal end portion 120 of device 100. The outer shaft 130 includes a window or opening 134 at a distal end 135 of the outer shaft 135. Window 134 is defined by an outer shaft cutting edge or cutter 132, which comprises cutting teeth 133. The outer shaft 130 may be rigid or malleable or combinations thereof and may be made of a variety of metals and/or polymers or combinations thereof, for example may be made of stainless steel. A distal portion 148 of the inner shaft 140 can be seen through the window or opening 134 of outer shaft 130. In FIG. 1, inner shaft 140 is depicted in a position such that an inner shaft cutting edge or cutter 141 (FIG. 3), comprising cutting teeth 143 is facing an inner wall (not shown) of outer shaft 130. Cutter 141 defines an inner shaft window or opening 154 (FIG. 3). Outer and inner shaft cutters 132 and 141 may move relative to one another in oscillation or rotation (or both) in order to mechanically cut tissue. For example, outer shaft cutter 132 may remain stationary relative to the hub 175 and button assembly 200 while the inner shaft cutter 141 may rotate about a longitudinal axis A of the device, thereby cutting tissue.

Rotation of inner shaft 140 may be achieved via manipulation of hub 175 (FIG. 1). that can orient the inner shaft 140 relative to the outer shaft 130 and may additionally allow for locking of the inner shaft relative to the outer shaft in a desired position, i.e., inner shaft may be locked in position when cutter 141 is facing down and electrode assembly 142 is facing up. As described above, hub 175 may be connected to a handle or handpiece 177 which may be controlled by an IPC 179. Alternatively, the hub 175 and/or handle portions may be manipulated manually. Inner shaft 140 may be selectively rotated to expose an electrode assembly 142 comprising electrodes 142a, 142b, through opening 134 of outer shaft 130, as shown in FIG. 2. Electrodes 142a, 142b may comprise electrode traces and the electrode traces may extend from the distal portion 148 of the inner shaft to a proximal end 151 (FIG. 10) of the inner shaft 140. As depicted in FIG. 2, inner shaft 140 is positioned such that the inner shaft cutter 141 is facing the interior (not shown) of outer shaft 130 and may be said to be in a downward facing direction and comprise a downward position. In the downward position, tissue is shielded from the inner shaft cutter 141 during hemostasis (via energy delivery through electrodes 142a, 142b), thereby delivering energy to tissue with no attendant risk that the cutting teeth 143 of the inner shaft 140 will diminish the efforts to achieve hemostasis. Device 100 may thus comprise two modes: a cutting or debridement mode and a sealing or hemostasis mode and the two modes may be mutually exclusive, i.e. hemostasis is achieved via energy delivery to tissue while cutters 132, 141 are not active or cutting. As described below, energy may be advantageously delivered simultaneously with a fluid such as saline to achieve an optimal tissue effect by delivering controlled thermal energy to tissue.

Figure 7:
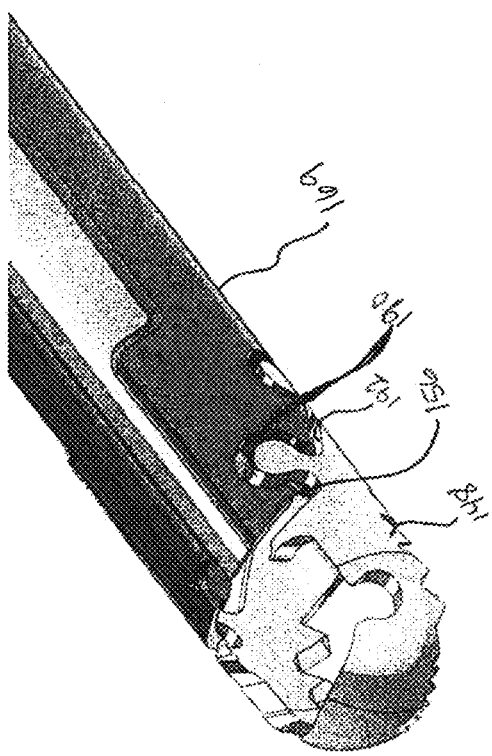
FIG. 7 is a perspective view of the distal end region of FIG. 6 with components removed.

As depicted in FIG. 3, when the inner shaft 140 is oriented such that the cutter 141 is in the downward position, rotating inner shaft 140 approximately 180 degrees relative to the outer shaft 130 will expose inner shaft cutter 141 and inner shaft opening 154 through the outer shaft opening 134. When the inner shaft cutter 141 is positioned as shown in FIG. 3, the inner shaft cutter 141 may be said to be in an upward position. The inner shaft opening 154 is fluidly connected to an inner shaft lumen 156, a portion of which can be seen in FIG. 7. Lumen 156 extends from the inner shaft distal portion 148 to the proximal end 151 (FIG. 10) of inner shaft 140 and may be fluidly connected with the suction source 172. With this configuration, tissue cut via inner and outer shaft cutters 141, 132 may be aspirated into the inner shaft lumen 156 through the inner shaft opening 154 upon application of suction source 172, thereby removing tissue from a target site.

Figure 4:
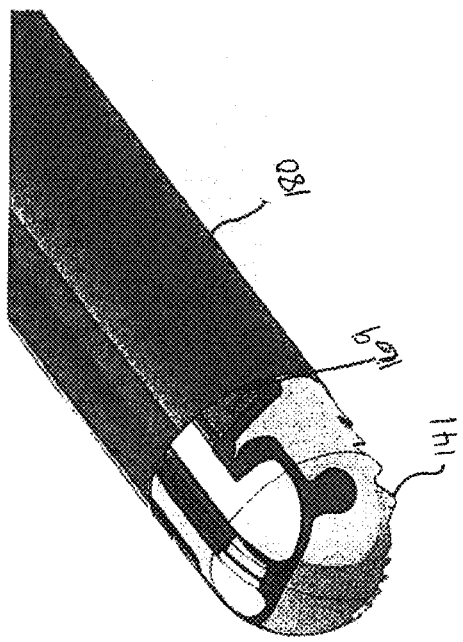
FIG. 4 is a perspective view the distal end region of FIG. 2 with an outer shaft removed to show portions of an inner shaft and insulation liner.
Figure 5:
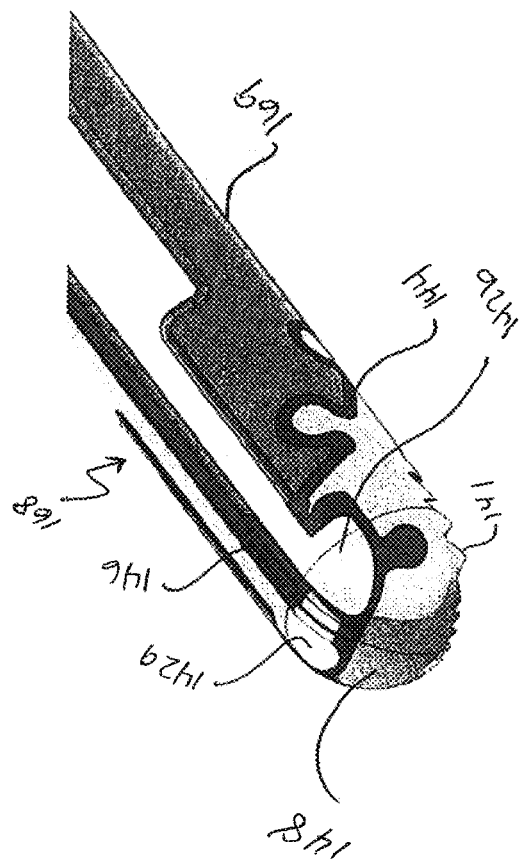
FIG. 5 is a perspective view of the distal end region of FIG. 4 with the insulation liner removed to show additional portions of the inner shaft and electrode traces.

With reference between FIGS. 4 and 5, the inner shaft 140 comprises a proximal assembly 168 including a proximal assembly shaft component 169 (more clearly seen in FIG. 5) and electrodes 142a and 142b. Inner shaft 140 also includes a joining assembly 144, which may be a non-conductive component and more specifically may comprise a liquid crystal polymer (LCP) overmold assembly. The joining assembly 144 may effectively join or connect the distal portion 148 of inner shaft 140 with the proximal assembly shaft component 169 (most clearly depicted in FIG. 5). Joining assembly 144 includes an extension portion 146 which aids in minimizing arc tracking from the electrodes 142a and 142b as will be further elucidated in the following discussion.

Electrodes or electrode traces 142a and 142b comprise bipolar electrodes and may comprise wet or dry electrodes. Electrodes 142a and 142b may be used to deliver any suitable energy for purposes of coagulation, hemostasis or sealing of tissue. Electrodes 142a and 142b are particularly useful with fluid such as saline provided by fluid source 152 (FIG. 1) which may be emitted near the outer shaft opening 134. Outer shaft opening 134 is fluidly connected to an outer shaft lumen 136, shown in phantom in FIG. 7. Lumen 136 extends from outer shaft opening 134 to the proximal end region 110 of device 100 and may be fluidly connected to the fluid source 152 (FIG. 1). Thus, fluid can be delivered to the opening 134 of outer shaft 130 and interacts with electrode traces 142a, 142b, as will be further described with reference to FIG. 1. In this manner, electrode traces 142a and 142b can advantageously provide Transcollation® sealing of tissue when used with the Transcollation® sealing energy supplied by the Aquamantys System, available from the Advanced Energy Division of Medtronic, Inc. With respect to "wet" RF coagulation technology, the technology for sealing tissue described in U.S. Pat. Nos. 6,558,385; 6,702, 810, 6,953,461; 7,115,139, 7,311,708; 7,537,595; 7,645, 277; 7,811,282; 7,998,140; 8,048,070; 8,083,736; and 8,361, 068 (the entire contents of each of which is incorporated by reference) describe bipolar coagulation systems believed suitable for use in the present invention. Other systems for providing a source of energy are also contemplated.

Both FIGS. 4 and 5 depict the distal end region 120 of device 100, with outer shaft 130 removed. FIG. 4 shows a portion of the inner shaft 140 coaxially maintained in an insulation liner or sheath 180. The liner 180 may extend from a location proximal the inner shaft cutter 141 and cutting teeth 143, along inner shaft 140, to the proximal end 151 of inner shaft 140. Liner 180 provides insulation between the inner and outer shafts 130, 140, thus providing electrical isolation of the electrodes 142a and 142b from outer shaft 130 as well as from one another while only adding a single, very thin layer to the overall device 100. Liner 180 may be made of any suitable material, for example, fluorinated ethylene propylene (FEP), polytetrafluoroethylene (PTFE), or any other material suitable as a non-conductive or electrically insulative material. Regardless, liner 180 is constructed so as to be negligible in its contribution to the overall diameter of the device 100 and particularly the distal end region 120 of the device 100.

Figure 6:
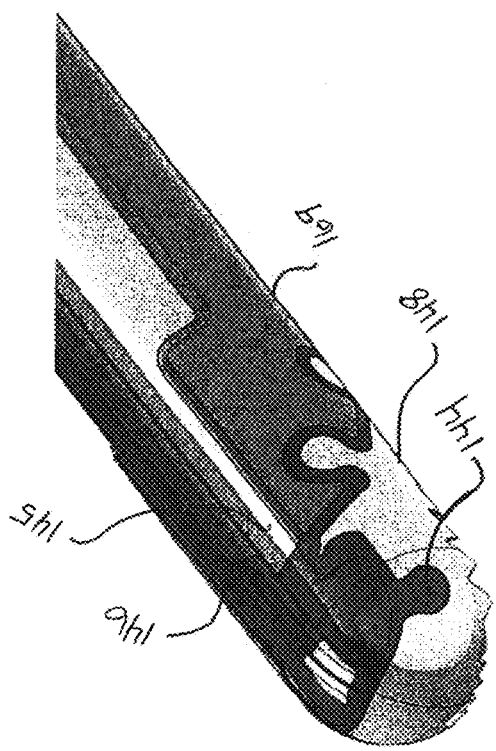
FIG. 6 is a perspective view of the distal end region of FIG. 5 with the electrode traces removed.

FIG. 5 shows the distal end region 120 of device 100 with both the outer shaft 130 and the insulation liner 180 removed, thus exposing only portions of inner shaft 140. As described above, inner shaft 140 includes a distal portion 148, which includes cutter 141, and an inner shaft proximal assembly 168 including proximal assembly shaft component 169. The individual distal portion 148 and shaft component 169 can be seen more clearly in FIG. 7 in which the joining assembly 144 and electrodes 142a, 142b are removed. The proximal assembly shaft component 169 may comprise a variety of suitable materials and for example, may comprise a liquid crystal polymer (LCP) extruded shaft component that is configured to support the placement of metallized conductors (e.g., electrodes 142a, 142b) and may support overmolding (e.g. of joining assembly 144) and/or a plating process, such as described below. Proximal assembly shaft component 169 may undergo a laser etching process to form the depressed areas 145 suitable for electrode placement or plating. Other methods of forming the depressed areas 145 are also contemplated. FIG. 6 shows inner shaft 140 with the electrodes or electrode traces 142a, 142b removed from the proximal portion 168 and joining assembly 144. Electrodes 142a and 142b may be formed on the proximal assembly shaft component 169 and on a portion of joining assembly 144 in a plating process for forming electrode traces. The portion over which the electrode traces may be applied includes depressed areas 145 (FIG. 6), which may be laser etched areas. One process of electrode plating may include first applying copper sufficient to conduct the desired power and then adding nickel and gold layers to the laser etched area 145. Other metals and combinations of metals are also contemplated, for example, silver may be used or any other metal or combination of metals effective in providing a cross section which meets power requirements for the energy delivery. Regardless, the plating process and overall electrode 142a, 142b thickness or depth is configured such that the electrodes 142a, 142b do not negatively impact the diameter of the device 100. As but one example, the electrode plating process may result in a dimensional change to the overall diameter as little as 0.0015".

FIG. 5 also more fully depicts joining assembly 144 which joins the distal portion 148 with the inner shaft proximal assembly 168 of the inner shaft 140. As seen in FIG. 5, portions of distal portion 148 and proximal assembly shaft component 169 may be configured in a "puzzle piece" arrangement as is indicated at joining assembly 144 which follows the lines of the puzzle piece. Each of the distal portion 148 and proximal assembly shaft component 169 include a mating edge 192, 190, respectively. This configuration distributes forces acting on the inner shaft 140 when the device 100 is in a cutting mode to aid in a secure coupling of the distal portion 148 and shaft component 169. The joining assembly extension portion 146 is located between electrodes 146a and 146b. This extension portion 146 provides adequate space between the electrodes 146a, 146b to mitigate arc tracking between the two and to improve the tissue depth effect.

Returning to FIG. 1, when fluid from fluid source 152 is provided through lumen 136 of the outer shaft 130, the fluid may travel between the outside diameter of the inner shaft 140 and the inside diameter of the outer shaft 130 to the distal end 120 of device 100. Fluid travels distally down the lumen 136 of outer shaft 130 and may "pool" in an area shown in FIG. 1 as essentially defined by the opening 134 of outer shaft 130. Likewise, electrodes 142a and 142b may be located slightly below the surface of the joining assembly 144 and/or the inner shaft proximal portion 168 (FIGS. 4, 5), creating another area for fluid pooling. This depressed electrode 142a, 142b surface can also prevent wear of the electrodes 142a, 142b. Pooling of fluid at the electrodes 142a, 142b allows for effective interaction between the fluid and the electrodes which in turn can provide effective and advantageous sealing of tissue, and in particular may provide effective Transcollation® sealing of tissue.

With continued reference to FIG. 1, electrodes 142a and 142b are situated in an area generally centrally located with respect to the outer shaft opening 134 when inner shaft cutter 141 is in a downward position. This generally central location of the electrodes 142a, 142b allows for energy delivery at an optimal point of debridement. In other words, after inner shaft cutter 141 and outer shaft cutter 132 are rotated or oscillated relative to one another to cut tissue, rotating inner shaft cutter 141 to the downward position to expose electrodes 142a, 142b and deliver energy through the electrodes 142a, 142b may allow for hemostasis in an area generally central to where debridement or cutting of tissue had taken place. The generally centered electrodes 142a, 142b allow for energy to essentially travel or radiate outwardly from the electrodes 142a, 142b to coagulate approximately the entire area of tissue previously cut. In other words, energy, and particularly RF energy may be provided at the center or near center of a portion of tissue previously cut or debrided.

Figure 8:
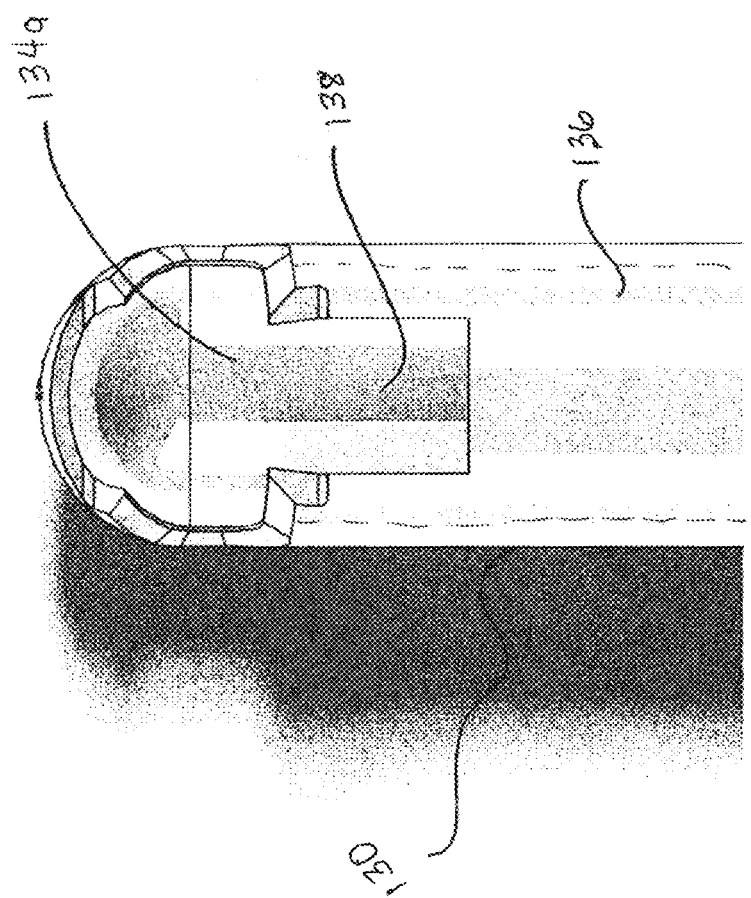
FIG. 8 is a perspective view of another embodiment of a distal end portion of an outer shaft of a device according the present invention.
Figure 9:
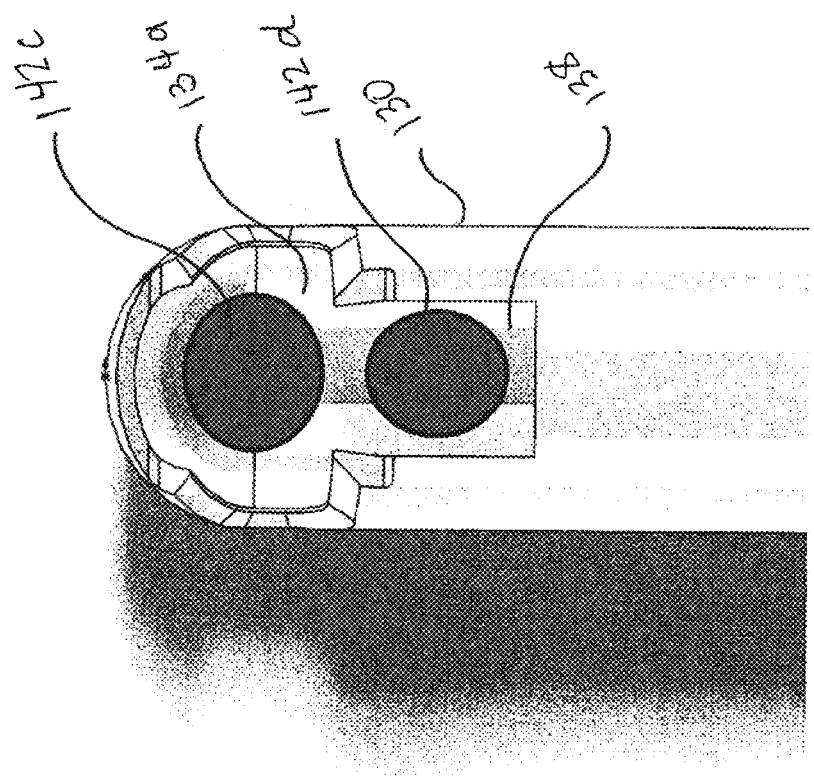
FIG. 9 is a perspective view the outer shaft of FIG. 8 showing a partial electrode configuration according to an aspect of the present invention.

FIGS. 8 and 9 depict an alternative outer shaft 130 and inner shaft 140 whereby an outer shaft window or opening 134a is essentially enlarged as compared to outer shaft window 134 (FIG. 2) via a proximal window portion 138. This enlarged opening 134a may afford an inner shaft 140 having significantly larger electrodes 142c, 142d, such as depicted in FIG. 9. Electrodes 142c, 142d may be otherwise constructed similar to electrodes 142a and 142b (e.g., FIG. 2) and the remaining portions of inner shaft 140 may be constructed as described above.

Figure 10:
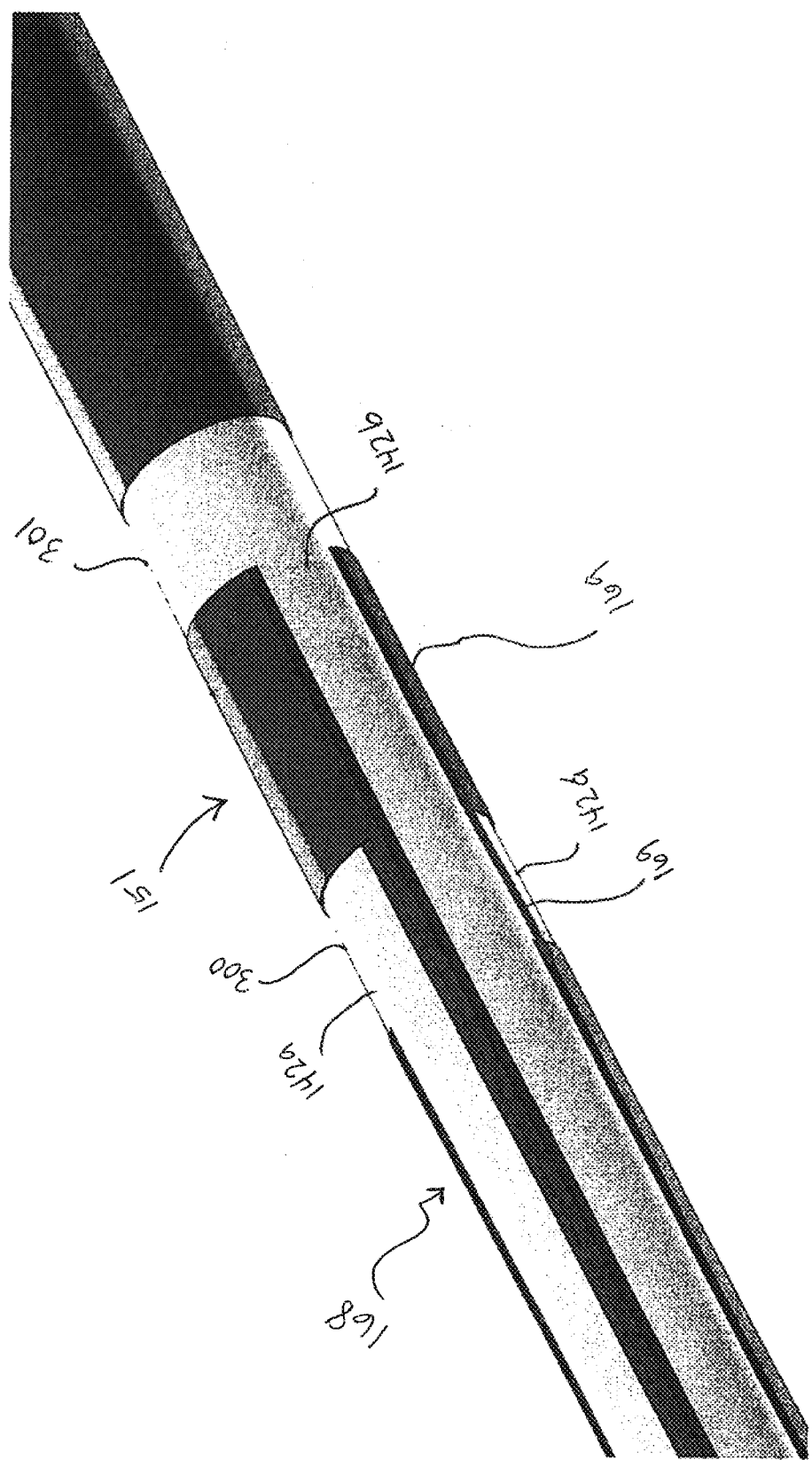
FIG. 10 is a perspective view of a proximal end of an inner shaft according to an aspect of the present invention.
Figure 14:
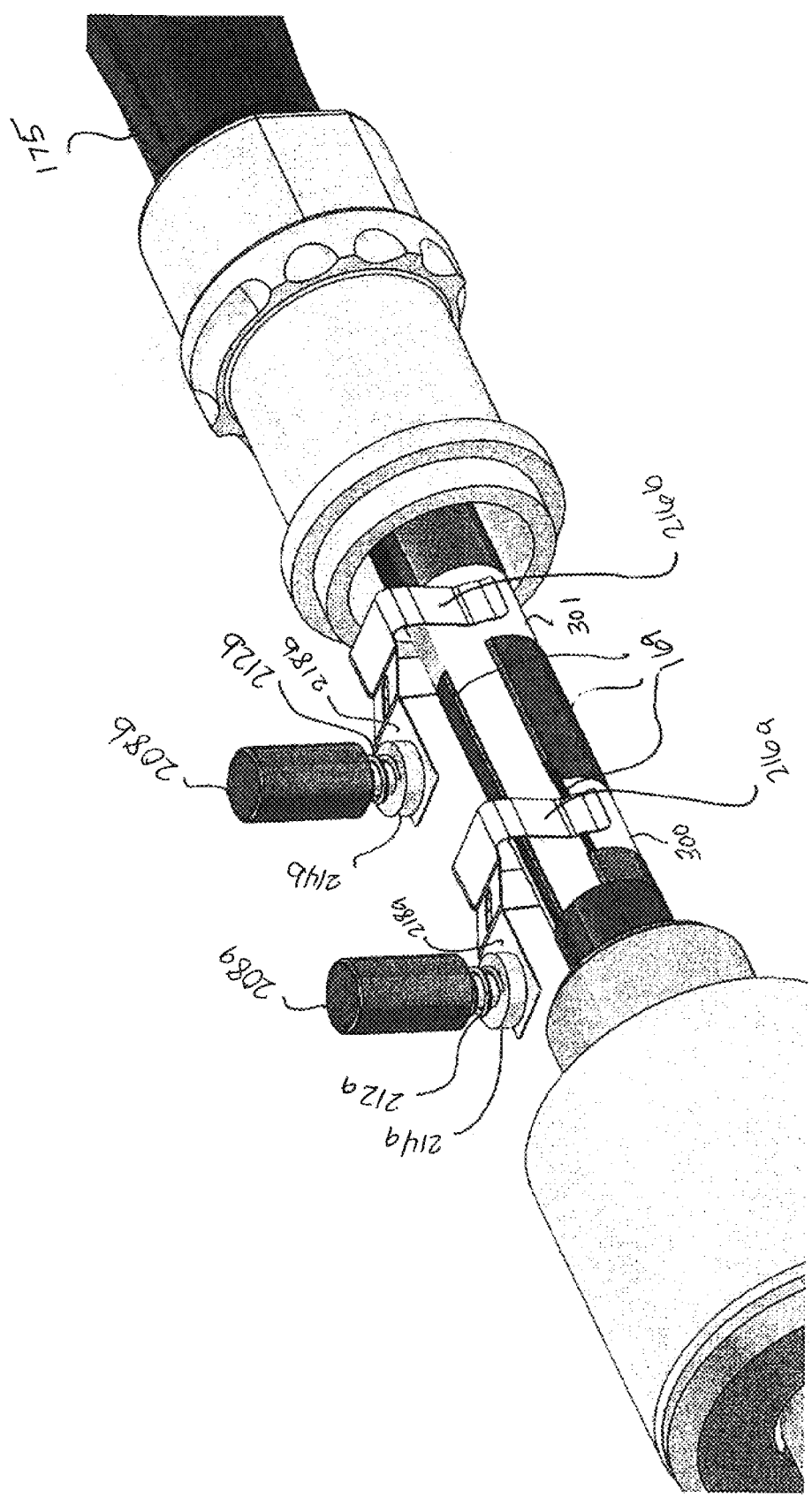
FIG. 14 is a perspective view of the assembly of FIG. 13 with portions removed according to an aspect of the present invention.

FIG. 10 depicts a section of proximal assembly 168 of inner shaft 140 which section, when assembled in device 100, is generally situated within button activation assembly 200 (FIG. 1). Electrodes 142a and 142b are shown as individual traces separated by proximal assembly shaft component 169, which isolates the electrode traces 142a, 142b from one another. Electrodes 142a includes a proximal portion comprising a partial ring 300 extending at least partially circumferentially around proximal assembly shaft component 169. Likewise electrode 142b comprises a proximal portion comprising a ring 301 which may extend fully circumferentially around proximal assembly shaft component 169 as depicted in FIG. 10. Rings 300 and 301 provide contact surface area for electrical contacts such as clips 216a, 216b (FIGS. 12, 14).

Figure 11:
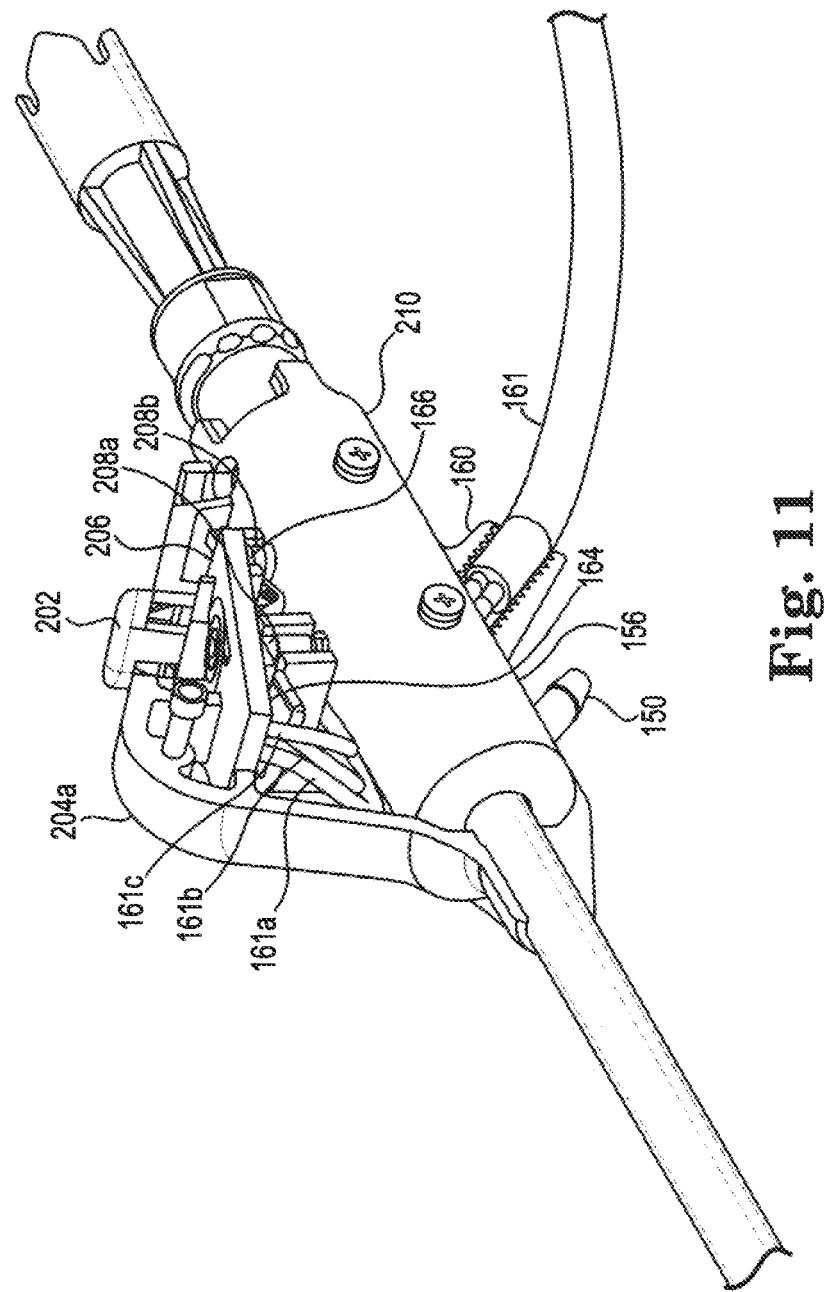
FIG. 11 is a perspective view of a proximal end of a device showing a button activation cell according to an aspect of the present invention.

FIGS. 11-14 depict the button activation assembly 200 and the way in which energy provided to electrodes 142a, 142b. FIG. 11 shows a partial cutaway view of the button activation assembly 200 one housing half 204b (FIG. 12) removed such that only housing half 204a is shown leaving portions of the button activation assembly 200 exposed. As shown in FIG. 11, at the proximal end region 110 of device 100 is provided a fluid housing 156 connected to the fluid connector 150 and an electrical contact housing 210 connected to the power source connector 160. The power source connector 160 is in turn coupled to a power cord or cable 161 comprising wires 161a, 161b and 161c. Power cord 161 is coupled to a printed circuit board (PCB) 206 via wires 161a, 161b and 161c. In addition, electrical contacts 164 and 166 electrically couple the power cord to caps 208a and 208b, as further explained with reference top FIGS. 12-14.

Figure 12:
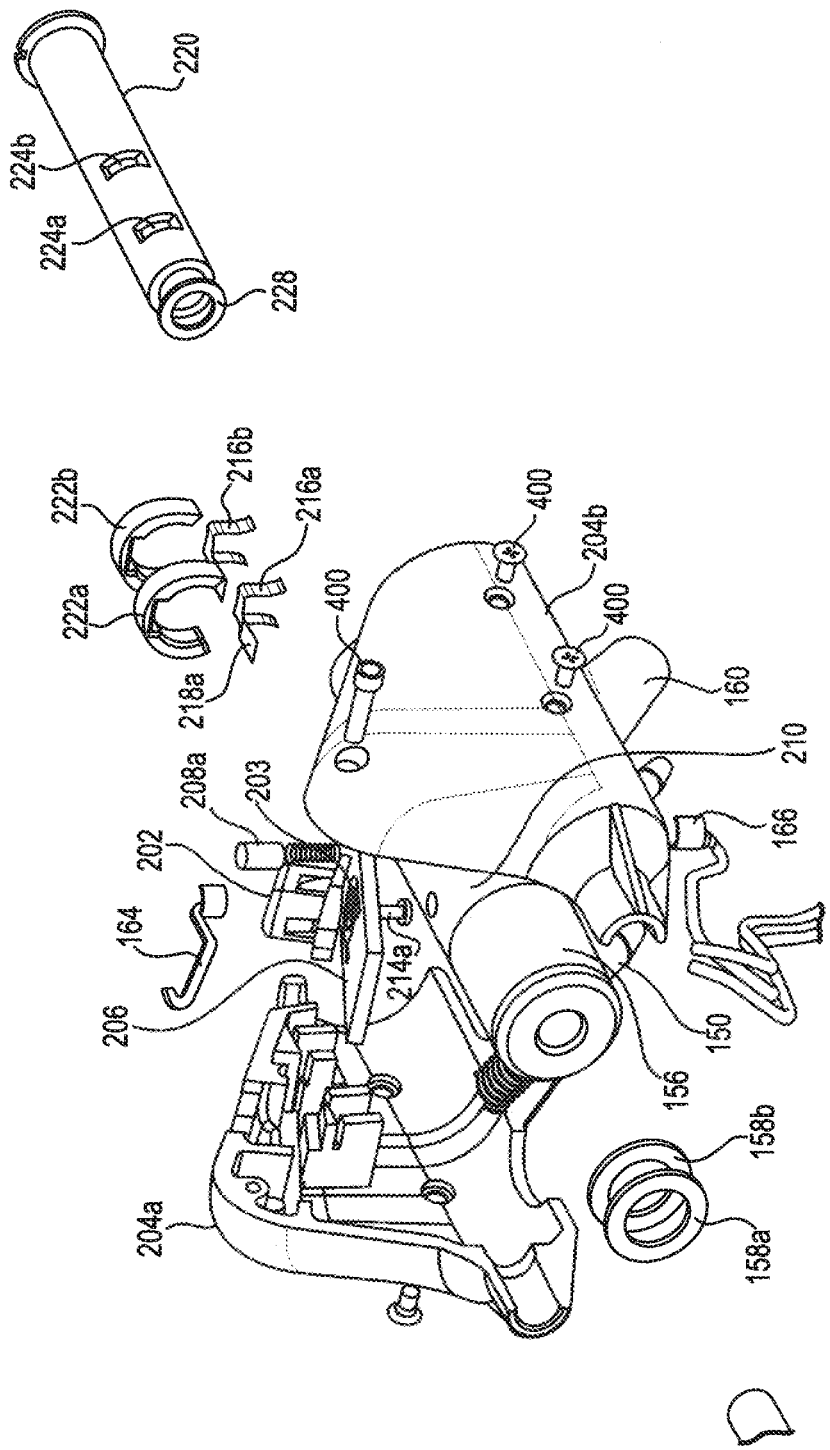
FIG. 12 is a an exploded view of the button activation cell of FIG. 11 according to an embodiment of the present invention.
Figure 13:
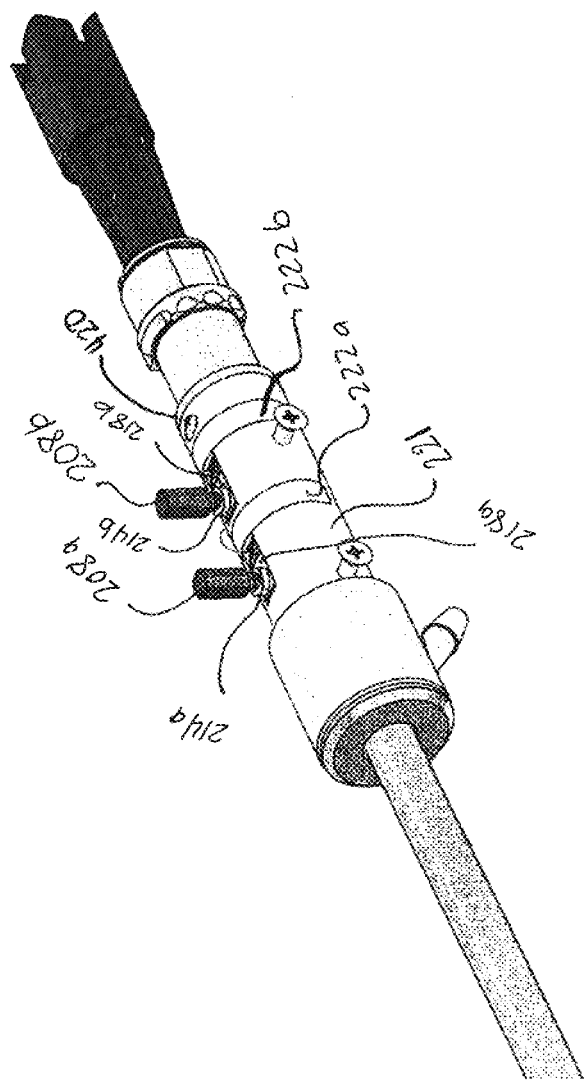
FIG. 13 is a perspective view of portions of the button activation cell of FIG. 11 according to an aspect of the present invention.

FIG. 12 shows and exploded view of the button activation cell 200 of FIG. 11 as well as a portion of proximal end region 110 with portions of the button activation cell removed. FIG. 13 shows an enlarged view of the portion of proximal end region 110 shown in FIG. 13 with still further portions removed. With reference between FIGS. 12-14, FIG. 12 shows two housing halves 204a and 204b which may be attached via any attachment device such as screws 400 and may, as described above, house various components of the button activation cell 200 as well as the fluid housing, electrical contact housing 210 and clip housing 220. Also depicted in FIG. 12 are o-rings 158a, 15b are adjacent fluid housing 156 and an o-ring 228 which is adjacent housing 220 for sealing fluid from the various components, including the electrical components provided in electrical contact housing 210.

Clip housing 220, shown alone or apart from cell 200 in FIG. 12, comprises two windows 224a, 224b. Clips 216a and 216b are provided in windows 224a, 224b with a flag 218a, 218b of each clip 216a and 216b viewable through or adjacent to windows 224a, 224b, such as depicted in assembled form in FIG. 13. Attached to clip housing 220 are two retaining rings 222a, 222b, for retaining the clips 216a and 216b in housing 220. As best seen in FIG. 14, post connectors 214a, 214b are coupled to clip flags 218a, 218b and provided on post connectors 214a, 214b are springs 212a, 212b. Over post connectors 214a, 214b and springs 212a, 212b are provided caps 208a, 208b. Also as best seen in FIG. 14, clips 216a and 216b are coupled to an in contact with rings 300 and 301 respectively of electrode traces 142a, 142b. Clips 216a, 216b, post connectors 214a,b, springs 212a, 212b and caps 208a, 208b are made of an electrically conductive material and provide electrical contact of the caps 208a, 208b to rings 300 and 301 when a source of power is activated or applied at caps 208a, 208b. As seen in FIGS. 11 and 12, the caps 208a, 208b are provided under the PCB 206, over which is provided button 202. Depressing button 202 drives a button contact assembly 203 which in turn moves to close circuitry of the PCB 206 allowing a pathway for current to flow from the power source 162 thus providing power to the electrodes 142a, 142b through the clips 216a, 216b as described above.

When energy is activated or applied to clips 216a, 216b, due to the intimate contact of clips 216a and 216b with electrode rings 300 and 301, electrical communication with bipolar electrodes 142a, 142b is achieved whereby energy is delivered along electrode traces 142a and 142b to the distal end 120 of device 100 and is applied to a targeted area of tissue as described herein above. This aspect of the present disclosure integrates electrodes 142a and 142b to the inner shaft 140 while isolating the inner shaft and electrodes 142a and 142b from other components and while distributing the required power to two separate and distinct electrodes 142a, 142b. This design also minimizes the number of layers required to make the distal end 120 of the device.

Figure 15:
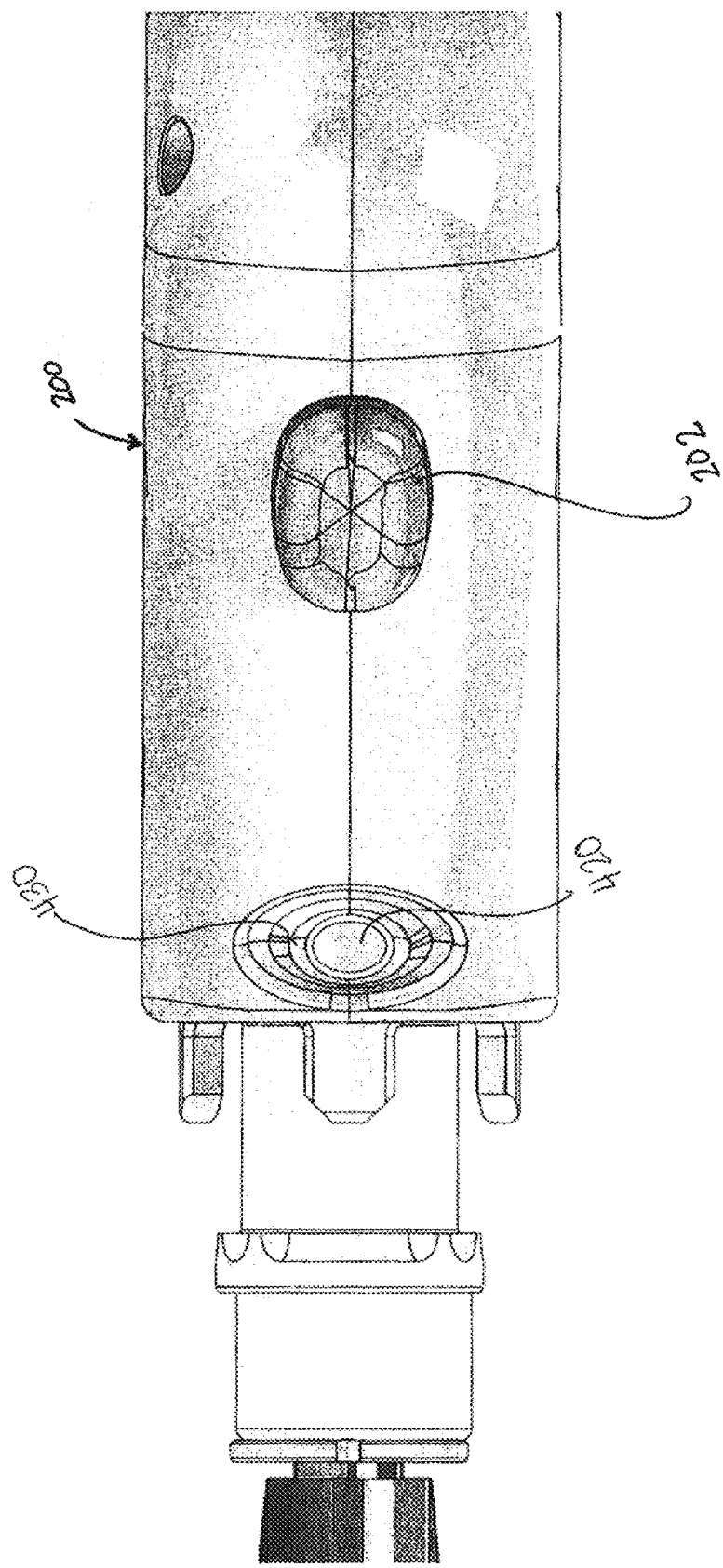
FIG. 15 is a top view of the button activation cell of FIG. 10 according to an aspect of the present invention.

FIG. 15 is a top view of the button activation assembly 200 and depicts an alignment fiducial 420 through a window 430 in housing 204. Alignment fiducial 420 is provided on housing 221 (FIG. 13). The alignment fiducial 420 is one of two fiducials which may be provided on device 100, with the second fiducial not shown. Alignment fiducials (e.g., 420) are provided as indicators of alignment of inner cutter 141 and may be colored to indicate a particular alignment configuration.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A method of surgically cutting and sealing tissue comprising:
  positioning a distal end region of a debridement device at an operative site within a patient, the debridement device having an outer shaft comprising a lumen and a distal end comprising a cutter forming a cutting window, the device further comprising an inner shaft rotatably disposed within the lumen of the outer shaft, the inner shaft having a distal portion comprising a cutter forming a cutting window, the outer shaft and the inner shaft forming a fluid passage therebetween, the device further comprising a bipolar electrode assembly including first and second electrodes that are electrically isolated from one another and positioned at the distal end region, the bipolar electrode assembly further including first and second electrical contacts coupled to the first and second electrodes, respectively, the device further comprising a proximal region opposite the distal end region and including housing maintaining a button, the button being manually transitionable to an activation position;
  grasping the housing by a hand of a user;
  cutting tissue at the operative site with the inner shaft cutter and the outer shaft cutter by moving the inner shaft relative to the outer shaft;
  transitioning the button to the activation position, including simultaneously completing an electrical pathway between each of the first and second electrical contacts and an energy source;
  delivering bipolar RF energy to the first and second electrodes in response to the button being held in the activation position to apply RF energy to tissue of the operative site; and
  terminating the delivery of bipolar RF energy to the first and second electrodes upon releasing the button from the activation position.

2. The method of claim 1, wherein the step of transitioning is performed by a finger of the user's hand otherwise simultaneously grasping the housing.

3. The method of claim 1, wherein the step of transitioning includes depressing the button relative to the housing.

4. The method of claim 1, further comprising discontinuing the delivery of bipolar RF energy when the button is manipulated away from the activation position.

5. The method of claim 4, wherein the button is provided as part of a button assembly, the button assembly further including a biasing member biasing the button away from the activation position.

6. The method of claim 1, wherein the button is operatively associated with first and second resilient members, and further wherein the activation position includes the first and second resilient members electrically coupled to the first and second electrical contacts, respectively.

7. The method of claim 6, wherein the first and second resilient members are located within the housing.

8. The method of claim 6, wherein the step of transitioning the button to the activation position includes establishing electrical communication between a source of energy and the first and second electrical contacts.

9. The method of claim 1, wherein the step of delivering bipolar RF energy includes effecting hemostasis at the operative site.

10. The method of claim 1, further comprising supplying fluid to the bipolar electrode assembly simultaneously with the step of delivering bipolar RF energy such that the fluid is operatively coupled to the bipolar electrode assembly.

11. The method of claim 10, wherein the step of supplying fluid to the bipolar electrode assembly includes delivering the fluid to the bipolar electrode assembly via the fluid passage.

12. The method of claim 1, wherein after the step of cutting tissue and prior to the step of transitioning the button, the method further comprising:
  arranging the debridement device in a home position in which the inner shaft cutter is shielded; and
  enabling an RF energy mode in which the debridement device is maintained in the home position.

13. The method of claim 12, wherein the step of delivering bipolar RF energy includes supplying bipolar RF energy while the RF energy mode is enabled.

14. The method of claim 12, wherein the cutter of the inner shaft includes a cutting surface at a perimeter of the inner shaft cutting window, and further wherein the home position includes the cutting surface disposed within the lumen of the outer shaft.

15. The method of claim 12, wherein the home position includes the outer shaft covering the inner shaft cutting window.

16. The method of claim 12, wherein the home position includes the cutter of the inner shaft facing a direction opposite the cutter of the outer shaft.

17. The method of claim 12, wherein the home position includes the first and second electrodes being exposed for electrically interfacing with tissue of the operative site.

18. A method of surgically cutting and sealing tissue comprising:
  positioning a distal end region of a debridement device at an operative site within a patient, the debridement device having an outer shaft comprising a lumen and a distal end comprising a cutter forming a cutting window, the device further comprising an inner shaft rotatably disposed within the lumen of the outer shaft, the inner shaft having a distal portion comprising a cutter forming a cutting window, the distal end region further comprising an electrode assembly, the outer shaft and the inner shaft forming a fluid passage therebetween;

cutting tissue at the operative site with the inner shaft cutter and the outer shaft cutter by moving the inner shaft relative to the outer shaft;

arranging the debridement device in a home position in which the inner shaft cutter is shielded;

enabling an RF energy mode in which the debridement device is maintained in the home position; and supplying RF energy to the electrode assembly while the RF energy mode is enabled to apply RF energy to tissue of the operative site.

19. The method of claim 18, wherein the cutter of the inner shaft includes a cutting surface at a perimeter of the inner shaft cutting window, and further wherein the home position includes the cutting surface disposed within the lumen of the outer shaft.

20. The method of claim 19, wherein the cutting surface includes a plurality of teeth each terminating at a tip, and further wherein the home position includes the tip of each of the plurality of teeth not being exposed at the outer shaft cutting window.

21. A method of surgically cutting and sealing tissue comprising:

positioning a distal end region of a debridement device at an operative site within a patient, the debridement device having an outer shaft comprising a lumen and a distal end comprising a cutter forming a cutting window, the device further comprising an inner shaft rotatably disposed within the lumen of the outer shaft, the inner shaft having a distal portion comprising a cutter forming a cutting window, the outer shaft and the inner shaft forming a fluid passage therebetween, the device further comprising a bipolar electrode assembly including first and second electrodes that are electrically isolated from one another and positioned at the distal end region;

cutting tissue at the operative site with the inner shaft cutter and the outer shaft cutter by moving the inner shaft relative to the outer shaft;

indicating a rotational relationship of the inner shaft relative to the outer shaft appropriate for provision of bipolar RF energy to the first and second electrodes; and supplying bipolar RF energy to the first and second electrodes to apply RF energy to tissue of the operative site.

* * * * *